United States Patent
Bhaskaran et al.

(10) Patent No.: US 11,390,547 B2
(45) Date of Patent: Jul. 19, 2022

(54) BACTERIAL CONSORTIUM FOR REDUCING PERCHLORATE AND/OR NITRATE AND THE PROCESS THEREOF

(71) Applicant: Council of Scientific and Industrial Research, New Delhi (IN)

(72) Inventors: Krishnakumar Bhaskaran, Thiruvananthapuram (IN); Anupama Vijaya Nadaraja, Thiruvananthapuram (IN)

(73) Assignee: COUNCIL OF SCIENTIFIC AND INDUSTRIAL RESEARCH, New Delhi (IN)

(*) Notice: Subject to any disclaimer, the term of this patent is extended or adjusted under 35 U.S.C. 154(b) by 1028 days.

(21) Appl. No.: 16/071,374

(22) PCT Filed: Dec. 30, 2016

(86) PCT No.: PCT/IN2016/050464
§ 371 (c)(1),
(2) Date: Jul. 19, 2018

(87) PCT Pub. No.: WO2017/125943
PCT Pub. Date: Jul. 27, 2017

(65) Prior Publication Data
US 2021/0147269 A1    May 20, 2021

(30) Foreign Application Priority Data
Jan. 19, 2016   (IN) .............................. 201611001839

(51) Int. Cl.
*C02F 3/34*   (2006.01)
*C12N 1/20*   (2006.01)
(Continued)

(52) U.S. Cl.
CPC ................ *C02F 3/341* (2013.01); *B09C 1/10* (2013.01); *C02F 3/30* (2013.01); *C12N 1/205* (2021.05);
(Continued)

(58) Field of Classification Search
CPC .. C02F 3/34; C02F 2101/163; C02F 2103/06; C02F 2103/10; C02F 3/341; C12N 1/205; C12R 2001/41; C12R 2001/07
(Continued)

(56) References Cited

U.S. PATENT DOCUMENTS

| | | | |
|---|---|---|---|
| 3,943,055 A | | 3/1976 | Korenkov et al. |
| 5,302,285 A | * | 4/1994 | Attaway ................... C02F 3/34 210/605 |

(Continued)

FOREIGN PATENT DOCUMENTS

| | | |
|---|---|---|
| WO | WO-2001036689 | 5/2001 |
| WO | WO-2005012192 | 2/2005 |

(Continued)

OTHER PUBLICATIONS

Singh et al, "Isolation and characterization of novel Serratia marcescens (AY927692) for pentachlorophenol degradation from pulp and paper mill waste" World J. Microbial Biorechnol 23, pp. 1747-1754 (Year: 2007).*

(Continued)

*Primary Examiner* — Claire A Norris
(74) *Attorney, Agent, or Firm* — Schwegman Lundberg & Woessner, P.A.

(57) ABSTRACT

The present invention discloses a novel microbial process for decontaminating (per)chlorate and/or nitrate containing matrices. A heterotrophic mixed microbial culture expressing the functional genes responsible for (per) chlorate and nitrate reduction is the major component of the process. The (Continued)

1-Contaminant reservoir, 2-Substrate reservoir,
3-pumping line, 4-Bioreactor, 5-Effluent out,
6-Biomass removal valve, 7 & 8-Pump, 9-Sample ports
10-packing material present process can be a better substitute for existing processes for decontaminating perchlorate contaminated propellant wastewater, ion exchange resin/regenerate solutions, etc. The consortium consists or comprises of *Halomonas* sp. NIIST-PRB-02 (MTCC No. 5911), *Bacillus* sp. NIIST-PRB-03 (MTCC No. 5912) and *Serratia marcescens* strain NIIST5 (MTCC No. 5821).

10 Claims, 3 Drawing Sheets

(51) Int. Cl.
| | |
|---|---|
| B09C 1/10 | (2006.01) |
| C02F 3/30 | (2006.01) |
| C12R 1/43 | (2006.01) |
| C12R 1/01 | (2006.01) |
| C12R 1/07 | (2006.01) |
| C02F 101/12 | (2006.01) |
| C02F 101/16 | (2006.01) |
| C02F 103/06 | (2006.01) |
| C02F 103/10 | (2006.01) |

(52) U.S. Cl.
CPC ...... *B09C 2101/00* (2013.01); *C02F 2101/12* (2013.01); *C02F 2101/163* (2013.01); *C02F 2103/06* (2013.01); *C02F 2103/10* (2013.01); *C02F 2305/06* (2013.01); *C12R 2001/01* (2021.05); *C12R 2001/07* (2021.05); *C12R 2001/43* (2021.05)

(58) Field of Classification Search
USPC .......................................................... 210/611
See application file for complete search history.

(56) References Cited

U.S. PATENT DOCUMENTS

| | | | |
|---|---|---|---|
| 5,948,260 A | 9/1999 | Attaway, III et al. | |
| 6,066,257 A | 5/2000 | Venkatesh et al. | |
| 6,077,429 A | 6/2000 | Frankenberger, Jr. et al. | |
| 6,077,432 A | 6/2000 | Coppola et al. | |
| 6,214,607 B1* | 4/2001 | Logan | C02F 3/34 |
| | | | 210/605 |
| 6,328,891 B1 | 12/2001 | Gaudre-Longerinas et al. | |
| 6,423,533 B1* | 7/2002 | Gearheart | B09C 1/10 |
| | | | 210/610 |
| 7,186,340 B1 | 3/2007 | Rittmann et al. | |
| 7,311,843 B2 | 12/2007 | Guter et al. | |
| 7,407,581 B2 | 8/2008 | Batista | |
| 7,575,686 B2 | 8/2009 | Sengupta et al. | |
| 7,931,807 B2 | 4/2011 | Bowman | |
| 2006/0292684 A1 | 12/2006 | Bentley et al. | |
| 2008/0042101 A1* | 2/2008 | Bryant | C12P 39/00 |
| | | | 252/175 |
| 2013/0149755 A1* | 6/2013 | Reed | C12M 29/08 |
| | | | 435/135 |
| 2017/0081226 A1* | 3/2017 | Breiner | C02F 3/305 |

FOREIGN PATENT DOCUMENTS

| | | |
|---|---|---|
| WO | WO-2007140150 | 12/2007 |
| WO | WO-2009156673 | 12/2009 |
| WO | WO-2010041041 | 4/2010 |
| WO | WO-2017125943 | 7/2017 |

OTHER PUBLICATIONS

"International Application No. PCT/IN2016/050464, Article 19 amendment received on Jul. 3, 2017", (Jul. 3, 2017), 11.

"International Application No. PCT/IN2016/050464, International Search Report and Written Opinion dated Apr. 11, 2017", (Apr. 11, 2017), 13 pgs.

Chung, Jinwook, et al., "Evaluation for Biological Reduction of Nitrate and Perchlorate in Brine Water Using the Hydrogen-Based Membrane Biofilm Reactor", Journal of Environmental Engineering, vol. 133, No. 2 (2007), (Feb. 2007), 157-164.

Nadaraja, Anupama Vijaya, et al., "Kinetics of chlorite dismutase in a perchlorate degrading reactor sludge", Environmental Technology, vol. 34, No. 16 (2013), (Aug. 1, 2013), 2353-2359.

Nadaraja, Anupama Vijaya, et al., "Perchlorate reduction by an isolated Serratia marcescens strain under high salt and extreme pH", FEMS Microbiol Lett 339:2 (2013) 117-121, (Feb. 1, 2013), 117-121.

Gingras, Tina M., et al., "Biological reduction of perchlorate in ion exchange regenerant solutions containing high salinity and ammonium levels", Journal of Environmental Monitoring 4(1):96-101, (Jan. 3, 2002), 96-101.

Wang, Chao, et al., "Kinetics of biological perchlorate reduction and pH effect", Journal of Hazardous Materials, vol. 153, Issues 1-2, May 1, 2008, pp. 663-669, (May 2008), 663-669.

* cited by examiner

1-Contaminant reservoir, 2-Substrate reservoir,
3-pumping line, 4-Bioreactor, 5-Effluent out,
6-Biomass removal valve, 7 & 8-Pump, 9-Sample ports
10-packing material

BACTERIAL CONSORTIUM FOR REDUCING PERCHLORATE AND/OR NITRATE AND THE PROCESS THEREOF

PRIORITY CLAIM TO RELATED APPLICATIONS

This application is a U.S. national stage filing under 35 U.S.C. § 371 from International Application No. PCT/IN2016/050464, filed on 30 Dec. 2016, and published as WO2017/125943 on 27 Jul. 2017, which claims the benefit under 35 U.S.C. 119 to India Application No. 201611001839, filed on 19 Jan. 2016, the benefit of priority of each of which is claimed herein, and which applications and publication are hereby incorporated herein by reference in their entirety.

FIELD OF THE INVENTION

The present invention relates to a bacterial consortium for reducing perchlorate and/or nitrate. It also relates to process for detoxifying (per)chlorate and/or nitrate containing matrices using the bacterial consortium. This process will find application in the bioremediation of liquid or solid matrices.

BACKGROUND OF THE INVENTION

Perchlorate ($ClO_4^-$) and chlorate ($ClO_3^-$) ions, together represented as (per)chlorate, are emerging environmental contaminants which are used in many industries especially in arms and ammunitions. Perchlorate interferes with the functioning of thyroid gland leading to hypothyroidism (reduced level of thyroid hormones, T3 and T4) and related metabolic and physiological disorders.

As per the World Health Organization (WHO) guidelines, the provisional maximum tolerable daily uptake (PMTDI) of $ClO_4^-$ in drinking water is 0.01 µg/kg body weight. United States Environmental Protection Agency (US EPA) has included $ClO_4^-$ as a priority pollutant and a permitted level for $ClO_4^-$ in drinking water is 15 µg/L. But in many US the permitted level is fixed well below the US EPA recommendation. Perchlorate has been detected in different matrices, such as soil, water, food products and human saliva in many countries.

Taking into account the toxicity and adverse impact of $ClO_4^-$ on environment, several approaches have been reported to remove/degrade (per)chlorate from water and soil. These methods can be broadly categorized into non-biological and biological The non biological methods include processes like ion exchange, reverse osmosis, electrodialysis, nanaofilteration, adsorption, electrochemical reduction, etc. However, all these processes are found to have limited applications due to non selectivity, high operational cost and requirement for secondary treatment strategy. Moreover, many of the physico-chemical processes only physically remove (no degradation to non-toxic chloride) (per)chlorate from the contaminated matrix.

On the other hand biological approaches (bioremediation) have been reported as environmental friendly, economic and effective for treating (per)chlorate. A major advantage of biological method for (per)chlorate treatment is the complete reduction of (per)chlorate to non-toxic chloride. Biological (per)chlorate removal can be in situ processes, ex situ processes or phytoremediation. In both in situ and ex situ processes dissimilatory (per)chlorate reducing bacteria (PRB) mainly involved in (per)chlorate reduction. Whereas, in phytoremedition, terrestrial or aquatic plants were used for removing perchlorate from soil or water respectively.

The PRB under anoxic condition utilize (per)chlorate as terminal electron sink, sequentially reducing it finally into chloride and oxygen. PRB are ubiquitous and these organisms are mainly utilized for detoxifying (per)chlorate in engineered biological systems and soil remediation sites.

Studies on the diversity of PRB, kinetics of PRB growth and (per)chlorate reduction, biochemical mechanism and genetics of (per)chlorate degradation have been well reported. PRBs are capable of using a wide variety of electron donors both organic and inorganic Most of the PRB's can also utilize alternate electron acceptors such as oxygen, nitrate and chlorate. The overall biochemical pathway involved in (per)chlorate reduction involves two key respiratory enzymes, perchlorate reductase which catalyze perchlorate and chlorate reduction and chlorite dismutase (C/d)) catalyzes the splitting of chlorite ($ClO_2^-$) into chloride and molecular oxygen.

The presence of functional genes perchlorate reductase and chlorite dismutase is a characteristics feature of PRBs. PRBs are phylogenetically diverse with members in all kingdoms, except eukaryotes. They are dominated by proteobacteria phylum ($\alpha$, $\beta$, $\gamma$ and $\epsilon$ subclasses), dominated by $\beta$ subclass.

Novel perchlorate reducing microbes (bacteria and archaea) have been continued to be reported from many environments, expanding their phylogenetic diversity. This will help to explore their physiological potential for application in bioremediation.

A number of studies have been reported (per)chlorate removal in bioreactor systems using different PRBs. Perchlorate laden waste/discharges like spent resin and regenerate solution can have salinity up to 15% (Chung et al., 2007) and pH either alkaline or acidic depending on the type of ion exchange resin and regenerate (like FeCl4−) used (Gingras and Batista, 2002; Chung et al. J. Environ. Eng., 2007, 133(2): 157; Gingras et al., J. Environ. Monitor, 2002, 4: 96-101.

The maximum salinity tolerance in PRMs reported so far was 11% by an acclimatized mixed culture and growth no was observed beyond this salinity (Logan et al., 2001).

Also studies reported so far has observed $ClO_4^-$ reduction within pH 5.0-9.0 only (Wang et al., 2008; Wang et al., J. Hazard. Mater., 2008, 153(1-2): 663-669.

Nitrate is reported as a co-occurring contaminant with perchlorate especially in agricultural regions and hence simultaneous removal of both is highly advantageous. Therefore, immense interest has been generated for an environment friendly and cost effective bioprocess for treating (per)chlorate and/or nitrate containing solutions under high salt and extreme pH conditions as disclosed in this patent.

Toxic oxy anions including perchlorate, chlorate, chlorite and/or nitrate reducing novel bacteria and processes using these organisms have been disclosed through a number patents as detailed below.

Biochemical reduction of perchlorate, chlorate and small amount of nitrate under anaerobic conditions using organic substrate by *Vibrio dechioraticans* Cuznesove B-1168 was disclosed in the U.S. Pat. No. 3,943,055. In this process, the nitrate reductase of the culture reduces perchlorate into chloride.

A method for treating propellant waste water using a bacteria HAP-1 was disclosed in U.S. Pat. No. 5,302,285. Process for perchlorate treatment using bacterium HAP-1 isolated from a sewage enrichment culture in a hydrogen gas lift reactor maintained at pH 6.5-8.0 are disclosed in U.S. Pat. Nos. 5,948,260, 5,302,285, 5,948,260.

Perchlorate and/or nitrate removal method from contaminated water and soil by a gram negative, facultative anaerobic bacterium-perciace was disclosed in U.S. Pat. No. 6,077,429.

Venkatesh et al. have reported a process for concentrating and destroying perchlorate and nitrate in aqueous solution in U.S. Pat. No. 6,066,257.

Using a mixed bacterial culture containing *Wolinella succinogenes*, biodegradation of energetic materials including perchlorate, nitrate, hydrolysate and other energetic materials was disclosed in U.S. Pat. No. 6,077,432.

The process for purifying water containing ammonium perchlorate using microbes belonging to groups consisting of *Pseudomonas, Micrococcus, Denitribacillus, Spirillum, Achroniobacter* was disclosed in the U.S. Pat. No. 6,328,891 B1.

Logan (2001) has reported perchlorate reduction using an oxidisable substrate by perchlorate respiring microorganisms in an anaerobic biofilm filtering system U.S. Pat. No. 6,214,607 B1.

The isolation and use of a bacterial strain DM-17 (close similarity with *Azoarens* sp. strain BS2-3) for perchlorate reduction was disclosed in patent No. WO 01/36689 A1 and U.S. Pat. No. 6,423,533 B1.

Biodegradation of oxyanions such as perchlorate load of ion exchange resins using mixed bacterial culture present in municipal anaerobic sludge, activated sludge and the BALI culture, *Wolinella succinogenes, Ideonella dechioratans* and *Acinetoacter thermotoleranticus* was disclosed in patent No. WO 2005/012192 A2.

Bently et al. (2006) have reported a method for treating oxidized contaminants including perchlorate, chlorate and chlorite using elemental sulphur as electron donor and either naturally occurring or inoculated microbial population (US 2009/0292684). Perchlorate reduction in water by hydrogen oxidizing bacteria was disclosed in U.S. Pat. No. 7,186,340 B1.

An improved method for destroying Perchlorate and other oxyanions of ion exchange resin through bioregeneration was disclosed in patent No. WO 2007/140150. The treatment of ion exchange resin loaded with Perchlorate was disclosed in U.S. Pat. No. 7,311,843 B2.

A method for biologically purifying aqueous solution containing ammonium perchlorate and optionally nitrate using perchlorate reducing bacteria utilizing organic carbonaceous substrate and nutritional elements was disclosed in patent No. WO 2009/156673. A mixed culture comprising of bacteria present in municipal anaerobic sludge, activated sludge and the BALI culture including *Wolinella succinogenes, Ideonella dechloratans, Acinetobacter thermotoleranticus*, strain CKB, strain PDA and KJ. The degradation of oxyanion like perchlorate on ion exchange resin was disclosed in the U.S. Pat. No. 7,407,581 B2. Reduction of perchlorate using elemental sulphur as electron donor and mollusk shells as alkalyting agent in a bioreactor by an autotrophic bacterium was disclosed in the U.S. Pat. No. 7,575,686.

Membrane biofilm reactor (MfBr) using autotrophic perchlorate reducing bacteria for removing perchlorate, nitrate and other organic contaminants was reported in U.S. Pat. No. 7,931,807 B2.

As it is apparent from above descriptions, there is an immediate requirement for improved processes and system for treating (per)chlorate and nitrate containing solutions or solid matrices.

Recently, we have reported a novel strain of bacteria exhibiting growth-coupled perchlorate reduction (Anupama et al., 2013). The bacterium was identified as *Serratia marcescens* strain. The bacterium reduced perchlorate completely with stoichiometric chloride build up. The presence of perA and cld genes coding for key respiratory enzymes involved in the perchlorate reduction was confirmed in the isolate. The isolate tolerated salinity up to 15% NaCl, wide range of pH (4.0-9.0), and it simultaneously reduced nitrate and perchlorate.

Compared to this isolated bacterium (which is part of the consortium), the consortium in the present patent has added advantages like it tolerated high initial perchlorate levels ($\geq 0.5$ g/L), facultative anaerobic nature, tolerance to high ammonium ($\geq 0.5$ g/L), as well as it can use a wide range of substrates. The properties of the present consortium like it can use wide substrate ranges, facultative anaerobic nature and high tolerance to perchlorate and ammonium will offer significant advantage especially for practical application.

OBJECTIVE OF THE INVENTION

1. The major objective of the present invention is a bioprocess for detoxifying (per)chlorate and/or nitrate containing matrices.
2. Another objective of the invention is a bioprocess for detoxifying (per)chlorate and/or nitrate containing matrices using a mixed bacterial culture essentially consisting of bacteria belonging to genii *Serratia, Halomonas* and *Bacillus*.
3. Another objective of the invention is a an improved bioprocess for detoxifying wide concentration range of (per)chlorate and/or nitrate containing matrices under high salt as well as wide pH conditions.

STATEMENT OF THE INVENTION

The present invention relates to a novel bioprocess for detoxifying (per)chlorate and/or nitrate containing matrices using a bacterial culture dominated by Genii belonging to—*Halomonas* sp. NIIST-PRB-02 (MTCC 5911), *Bacillus* sp. NIIST-PRB-03 (MTCC 5912) and *Serratia marcescens* strain NIIST5 (MTCC 5821) under specified conditions.

Through this process, liquids or solid matrices containing (per)chlorate and/or nitrate under high salt and wide pH conditions can be treated.

DETAILED DESCRIPTION OF THE INVENTION

Figure 1:
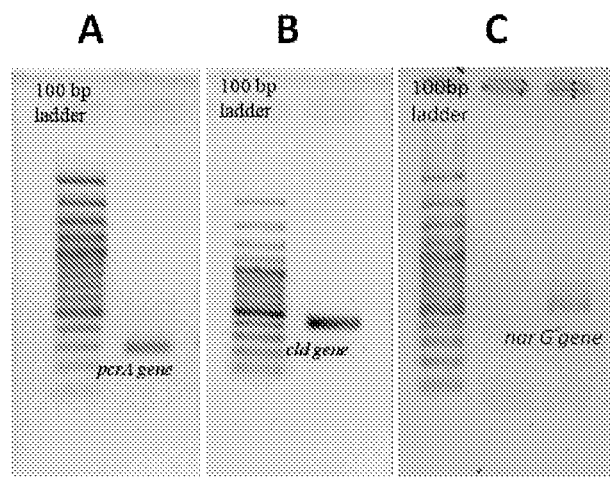
FIG. 1. Agarose gel image showing A) 100 bp ladder (lane 1), amplified per A (lane 2); B) 100 bp ladder (lane 1), amplified Cld gene (lane 2); C) 100 bp ladder (lane 1), amplified narG gene (lane 2).

The present invention relates to a novel bioprocess for detoxifying (per)chlorate and/or nitrate containing matrices using a mixed bacterial culture dominated by genii belongs to—*Halomonas* sp. NIIST-PRB-02 (MTCC 5911), *Bacillus* sp. NIIST-PRB-03 (MTCC 5912) and *Serratia marcescens* strain NIIST5 (MTCC 5821) under specified conditions.

Through this process, liquids or solid matrices containing (per) chlorate and/or nitrate at wide concentration ranges and under high salt and wide pH levels can be decontaminated.

This process can find application for treating perchlorate and nitrate contaminated water, propellant wastewater, ion exchange resin regenerate solution, etc.

The present invention discloses a novel bioprocess for detoxifying (per)chlorate and/or nitrate containing solutions or solid matrices using a mixed bacterial culture (consortium) dominated by bacteria essentially consisting of genii *Halomonas*, *Bacillus* and *Serratia*. This invention comprises mainly two components, (1) the specific bacterial consortium and (2) the process for decontaminating (per) chlorate and/or nitrate contaminated matrices. The following description addresses both.

(1) Bacterial Consortium Reducing (Per) Chlorate and/or Nitrate:

The present consortium consists mainly of three bacteria belongs to genii *Halomonas*, *Bacillus* and *Serratia*. The cultures of these three strains were deposited at MTCC with the following details—*Halomonas* sp. NIIST-PRB-02 (MTCC 5911), *Bacillus* sp. NIIST-PRB-03 (MTCC 5912) and *Serratia marcescens* strain NIIST5 (MTCC 5821). All three bacteria in the consortium can be cultured and maintained together or individually. All the bacteria expresses the genes specific for the reduction of (per) chlorate and/or nitrate, so that this consortium can be effectively used for treating liquid/solid matrices contaminated with (per)chlorate and/or nitrate. This consortium is facultative anaerobic so that it can work under both aerobic and anoxic condition.

The consortium can be applied for (per)chlorate and nitrate reduction in batch cultures or in continuously fed bioreactors. Moreover, the consortium can be maintained in an engineered biological system (bioreactor) either as suspended biomass or attached to inert substrates to form a fixed film. The consortium can tolerate high concentration of perchlorate (up to 5.0 g/L), high salt (>15%), high ammonium (0.5 g/L) and extreme pH (4-9) which makes it ideal for decontaminating ion exchange regenerate solution.

The consortium utilizes organic substrates for growth including sugars, organic acids, alcohols etc. However, it prefers acetate as the electron donor for reducing perchlorate into chloride and oxygen.

(2) Process for Reducing (Per)Chlorate and/or Nitrate:

In the present process, (per)chlorate and/or nitrate contaminated matrix (liquid or solid) will be exposed to the above described bacterial consortium for a specific period of time under anoxic environment in a suitable bioreactor system.

To support the bacterial activity an organic substrate and nutrients will be provided to the reactor. Under such condition the consortium will use organic substrate as electron donor and (per)chlorate and/or nitrate as electron acceptor and reduces the latter into non-toxic chloride, oxygen or nitrogen.

In this process the bacterial system can be maintained either as suspended (fluidized) biomass or fixed film on inert substrates like plastic, clay, glass etc.

The process can be used for treating wastewater or solutions or solid matrix contaminated with (per) chlorate and/or nitrate.

Thus the Present invention provides bacterial consortium useful for detoxifying (per) chlorate and/or nitrate essentially consist of *Halomonas* sp. NIIST-PRB-02 (MTCC 5911), *Bacillus* sp. NIIST-PRB-03 (MTCC 5912) and *Serratia marcescens* strain NIIST5 (MTCC 5821).

In an embodiment, a bioprocess for detoxifying (per) chlorate and/or nitrate containing matrices using a bacterial consortium wherein the said process comprising the steps of:
  a. maintaining the bacterial consortium and providing substrate/nutrients for sustaining the microbial activity in a bioreactor;
  b. contacting (per)chlorate and/or nitrate contaminated matrix with the bacterial consortium in the bioreactor of step (a) at redox potential below −200 mV, neutral pH and 30±5° C. for a period ranging between 3 to 12 h to obtain detoxified matrices.

In yet another embodiment, in a process, bacterial consortium of bacteria belongs to genii *Serratia*, *Halomonas* and *Bacillus* isolated from salt adapted sludge from a bioreactor and has been deposited with MTCC having *Halomonas* sp. NIIST-PRB-02 (MTCC 5911), *Bacillus* sp. NIIST-PRB-03 (MTCC 5912) and *Serratia marcescens* strain NIIST5 (MTCC 5821).

In yet another embodiment, bacteria are maintained in suspension or attached to a suitable inert surface like glass, plastic or ceramic for sustained activity.

In yet another embodiment, wherein (per)chlorate and/or nitrate containing matrices in propellant wastewater containing perchlorate, ammonia, high salt and acidic or alkaline pH or solid matrices having salinity up to 15% and pH in the range 4 to 10 and perchlorate up to 5 g/L can be decontaminated.

In yet another embodiment, nutrients in step (a) is mineral salt medium containing (g/L water) $K_2HPO_4$-0.22, $KH_2PO_4$-0.22, $(NH_4)_2SO_4$-0.22, $MgSO_4.7H_2O$-0.05, $CaCO_3$-0.005, $FeSO_4.7H_2O$-0.005, $KClO_4$-1.5 g/L and trace metal solution-1.0 ml.

In yet another embodiment, reduction of perchlorate is in the range of ≥5 g/L.

In yet another embodiment, reduction of nitrate is in the range of ≥5 g/L.

In yet another embodiment, reduction of nitrate and perchlorate using mixed bacterial culture was carried out optionally in the presence of ammonium.

In yet another embodiment, reaction using bacterial consortium was carried out in the presence of (per)chlorate and/or nitrate ≥5 g/L concentration.

The following examples serve to provide the best modes of practice for the present invention, and should not be constructed as limiting the scope of the invention:

Example 1: The Bacterial Consortium; its Characteristics, Preparation and Maintenance The bacterial consortium (mixed culture) used in the present process was dominated by bacteria belongs to *Halomonas* sp. NIIST-PRB-02 (MTCC 5911), *Bacillus* sp. NIIST-PRB-03 (MTCC 5912) and *Serratia marcescens* strain NIIST5 (MTCC 5821). All three bacteria were isolated from a laboratory scale bioreactor for reducing (per) chlorate and/or nitrate.

The consortium can be grown and maintained in mineral salt medium containing (g/L water) $K_2HPO_4$-0.22, $KH_2PO_4$-0.22, $(NH_4)_2SO_4$-0.22, $MgSO_4 \cdot 7H_2O$-0.05, $CaCO_3$-0.005, $FeSO_4 \cdot 7H_2O$-0.005, $KClO_4$-1.5 g/L and trace metal solution-1.0 ml. A higher perchlorate to acetate ratio like 1:2 was required for complete reduction of (per)chlorate and/or nitrate. The consortium can be maintained under both aerobic and anoxic conditions.

Under optimum conditions of pH (~7), temperature (30±3° C.) and anoxic condition, the specific growth rate (μ) of the consortium was 0.025/h in the above media. Alternatively, the consortium can be developed and maintained in nutrient broth or Luria Bertani media.

The consortium was screened for its potential to reduce perchlorate and/or nitrate. This was done by analyzing the presence of metabolic genes responsible for perchlorate and/or nitrate. Polymerase chain reaction (PCR) with specific primers for perchlorate reductase (perA gene) and chlorite dismutase (cld gene) involved in the complete degradation of perchlorate was done. The gene product obtained was sequenced and it was confirmed through similarity check using BLAST (NCBI) algorithm. Similarly the presence of nitrate reductase (narG) gene was also confirmed. The PCR images were presented in FIG. 1.

The present consortium was able to reduce both perchlorate and nitrate simultaneously under anoxic condition using acetate as substrate (electron donor). It was able to tolerate and reduce perchlorate at ppb (μg/L level) to g/L level.

Example 2: Reduction of Perchlorate in Discharge Brine Using the Consortium in Batch Culture The present consortium was tested for reducing perchlorate present in an industrial discharge brine (effluent). Effluent collected from an ammonium perchlorate (rocket fuel) manufacturing unit was used for the treatment study. The effluent had perchlorate-70 g/L, ammonium-17.9 g/L, salinity 5%, pH-6.0 and TOC-9.46 mg/L. This effluent was diluted with water to bring down the perchlorate and ammonium concentration as well as salt level.

Batch experiment was conducted with diluted industrial brine ($ClO_4^-$ at 100-500 mg/L level). The consortium acclimatized to 5% NaCl was used for the treatment study. This was done by slow adaptation of the consortium to high salt conditions. The batch experiment was conducted in 25 ml capacity crimp cap vials. The mineral medium as described in example 1 (except the level of $KClO_4$ and $CH_3COONa$), was used in the experiment. Dissolved oxygen in the medium was expelled by sparging air free nitrogen from a cylinder filtered through 0.22 μm filters (Millipore) for 10 min. The vials were incubated under at 30±3° C. for a period of 72 h The consortium from an anoxically grown culture at late log phase was pelletized (8000×g), washed and resuspended in deaerated mineral medium in the vial (initial $OD_{600}$ 0.03-0.05). The vials were incubated under at 30±3° C. and samples were withdrawn using a syringe every 12 h for estimating $ClO_4^-$, $Cl^-$ and $OD_{600}$.

Perchlorate and chloride were estimated through IC (Dionex-1100) with AS 11 column and anion self-regenerating suppressor (ASRS 300, 4 mm) with $NaCO_3:NaHCO_3$ (1:4.8 mM) buffer as mobile phase at flow rate of 1.5 mL/min.

Figure 2:
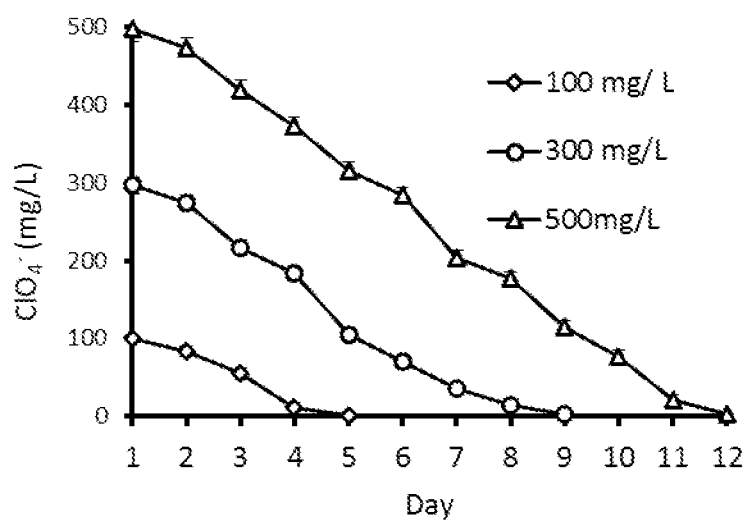
FIG. 2. Perchlorate reduction profile of diluted industrial effluent containing different initial $ClO_4^-$ concentration at 5% NaCl by the present consortium.

Reduction of perchlorate present in an industrial discharge containing high salt and ammonia is presented in FIG. 2. It is demonstrated that the present consortium can be used for treating perchlorate contaminated effluents under high salt and in presence of ammonium.

Figure 3:
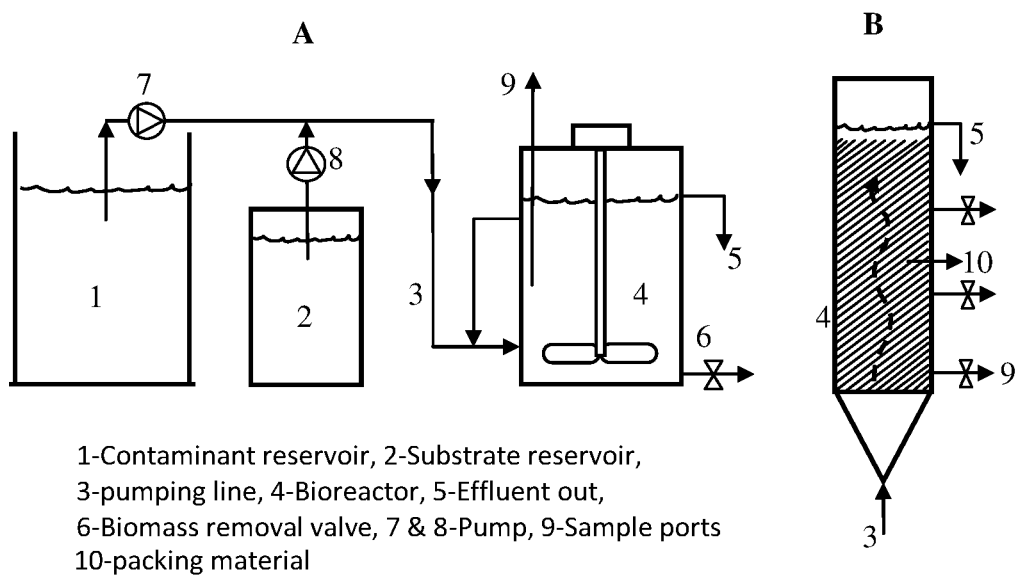
FIG. 3. Schematic representation of the process for decontaminating (per)chlorate and/or nitrate contaminated water (A) bioreactor with suspended biomass; (B) fixed film type bioreactor.

Example 3: Decontamination of Perchlorate in Water Using the Consortium in Continuous Bioreactors A process flow chart for decontaminating perchlorate in a contaminated aqueous system using the present bacterial consortium is presented in FIG. 3. The bacterial consortium was maintained as a suspended biomass in a 3 Lit capacity glass tank (working volume 2.5 lit). Totally anoxic atmosphere inside the reactor was created initially by sparging with air free nitrogen for 10 min. The biomass load level in the reactor was equivalent to around 10 g dry weight. Slow mixing of the biomass was done using an impeller. The temperature in the reactor was at 30±3° C. The bacterial growth inside the reactor was supported through providing a nutrient solution as specified in example 1.

Water containing perchlorate at 10 mg/L was stored in a plastic reservoir. It was introduced into the bioreactor using a peristaltic pump (Watson-Marlow). The nutrient solution was mixed with the influent before introducing into the reactor. The perchlorate contaminated water during its retention inside the reactor will be used by the consortium and reduces it into non-toxic chloride and oxygen. The treated effluent will be collected and it was analyzed for residual perchlorate and chloride build up. Perchlorate and chloride were analyzed using a DIONEX ion chromatographic system using DIONEX AS16 column, anion suppressor and 50 mM NaOH mobile at 1 ml/min. During this experiment, complete reduction of perchlorate was observed.

Alternatively, a fixed film type bioreactor was also used for treating perchlorate contaminated water. An acrylic column of 4.5 cm internal diameter and 60 cm height was used for making the bioreactor. Up to 40 cm height, inert media like plastic rings or glass beads was used as surface for the biofilm growth. The reduction of perchlorate was similar to the suspended growth system.

Example 4: Simultaneous Reduction of Perchlorate and Nitrate by the Consortium

The simultaneous reduction of nitrate and perchlorate by the present consortium was demonstrated in batch cultures. The experiment was conducted in 25 ml capacity crimp cap vials. The mineral medium as described in example 1 (except the level of perchlorate and acetate), was used in the experiment. Dissolved oxygen in the medium was expelled by sparging air free nitrogen from a cylinder filtered through 0.22 μm filters (Millipore) for 10 mins. The consortium from an anoxically grown culture at late log phase was pelletized (8000×g), washed and resuspended in deaerated mineral medium in the vial (initial $OD_{600}$ 0.03-0.05). The vials were incubated under at 30±3° C. and samples were withdrawn using a syringe every 12 h for a period of 72 h for estimating $ClO_4^-$, $Cl^-$ and $OD_{600}$. Perchlorate and chloride were estimated through IC (Dionex-1100) with AS 11 column and anion self-regenerating suppressor (ASRS 300, 4 mm) with $NaCO_3:NaHCO_3$ (1:4.8 mM) buffer as mobile phase at flow rate of 1.5 mL/min.

Figure 4:
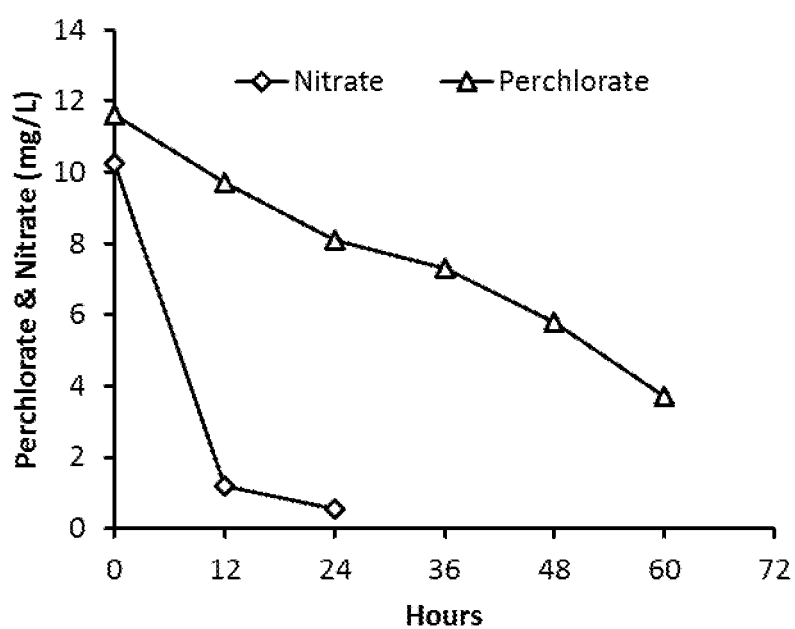
FIG. 4. Reduction of perchlorate alone and perchlorate-nitrate mixture by the present consortium in batch culture.

Nitrate (as $KNO_3$; 10 mg/L $NO_3^-$) was added to the inorganic mineral medium containing perchlorate and acetate (10 mg/L and 20 mg/L respectively). Nitrate free positive control and heat killed (non biological) controls were run parallel. It was found that both nitrate and perchlorate were reduced simultaneously. However, nitrate was reduced more rapidly compared with perchlorate. The result of the present study is given in the FIG. 4.

Example 5: Perchlorate Reduction in Presence of Ammonium

The present consortium was tested for perchlorate reduction activity in presence of ammonium at various initial concentrations. The experiment was conducted in 25 ml capacity crimp cap vials using the mineral salt medium as described in example 1. Ammonium was added to the medium as ($NH_4OH$) at different levels to bring the final ammonium concentration in the range 100-800 mg/L. pH of the medium was subsequently adjusted to neutral range by adding 0.1M HCl. The vials were incubated under at 30±3° C. for a period of 72 h and samples were withdrawn using a syringe every 12 h for estimating $ClO_4^-$. Perchlorate was estimated through IC (Dionex-1100) with AS 11 column and anion self-regenerating suppressor (ASRS 300, 4 mm) with $NaCO_3:NaHCO_3$ (1:4.8 mM) buffer as mobile phase at flow rate of 1.5 mL/min.

Figure 5:
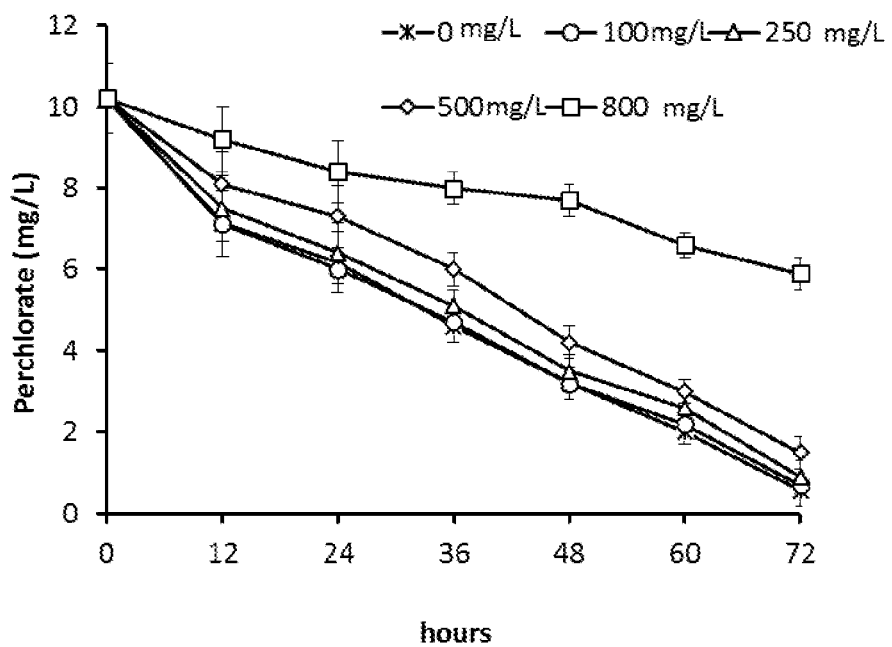
FIG. 5. Reduction of perchlorate in presence of ammonium at different initial concentration in batch culture.

A significant $ClO_4^-$ reduction (above 85%) was observed at $NH_4^+$ concentrations up to 500 mg/L. However further increasing ammonium to 800 mg/L resulted in decline in reduction to 41%. The result of the study is presented in FIG. 5.

Example 6: Facultative Anaerobic Consortium Capable of Reducing Perchlorate

Figure 6:
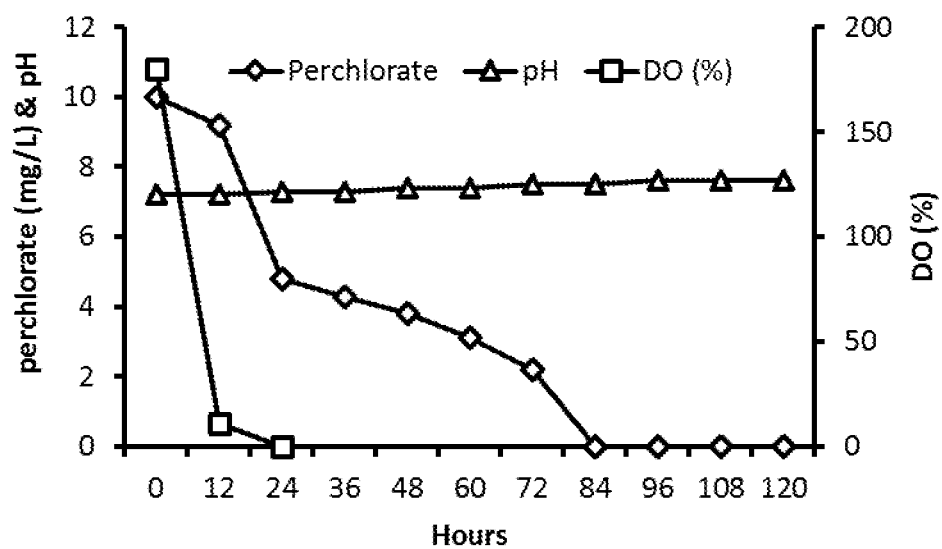
FIG. 6. Reduction profile of perchlorate in a mini-fermenter using the consortium developed under aerobic conditions.

The facultative anaerobic nature of the present consortium was tested in a 500 ml capacity mini-fermenter (Applikon). The consortium from a stock was inoculated in Nutrient broth medium (100 ml) in a 500 ml conical flask and incubated under aerobic conditions in a rotary shaker (150 rpm) for 48 h under ambient temperature. After 48 h the pellet was separated by centrifugation, washed with sterile mineral salt medium and re-suspended in the mineral salt medium which is used as the inoculum (50 ml). Around 400 ml of mineral salt medium added with perchlorate at 10 mg/L level and acetate at 30 mg/L was taken in the fermenter vessel and incubated under anoxic condition with continuous mixing (100 rpm) and at 30° C. Dissolved oxygen and pH are continuously monitored. Samples were withdrawn very 12 h to estimate residual perchlorate in the medium. It was observed the dissolved oxygen in the medium dropped to zero in <12 h and subsequently perchlorate reduction initiated slowly, and perchlorate level came to undetectable level after 72 h. The initial lag in reduction of perchlorate was due to the presence of residual oxygen in the medium. The bacterial cells start consuming perchlorate when dissolved oxygen is completely exhausted. In the present experiment the consortium was developed under aerobic condition, its perchlorate reduction property was not found affected when it was subsequently incubated under anoxic condition (facultative anaerobic). The data of the experiment is presented in FIG. 6.

Major Advantages of the Invention:
1. The present process using the mixed microbial system can be used for decontaminating perchlorate in wide concentration range from ppb (microgram/L) level to g/L level.
2. The mixed microbial system in the present process for decontaminating perchlorate can tolerate ammonia, so that it can be used for treating propellant wash water containing perchlorate and ammonia.
3. The present process using the mixed microbial system can be used for decontaminating wastes containing simultaneously (per)chlorate and/or nitrate.
4. The present process can be used for treating (per) chlorate and/or nitrate containing solutions at wide range of pH (acidic to alkaline) and high salt conditions.
5. The mixed microbial culture in the present process is facultative anaerobic so that it can be maintained under aerobic and anoxic conditions.

We claim:

1. A bioprocess for detoxifying (per)chlorate and/or nitrate containing matrices using a bacterial consortium, said process comprising:
   (a) maintaining a bacterial consortium and providing a substrate and nutrient broth and conditions for sustaining microbial activity of the consortium; and
   (b) contacting a (per)chlorate and/or nitrate contaminated matrix with the bacterial consortium at a redox potential below −200 mV, neutral pH and 30±5° C. for a period ranging between 3 to 36 h to obtain a detoxified matrix, wherein the nitrate concentration before contacting is ≥5 g/L;
   wherein said bacterial consortium consists of bacteria having Accession No. MTCC No. 5911, MTCC No. 5912, and MTCC No. 5821.

2. The bioprocess as claimed in claim 1, wherein the bacteria are maintained in suspension or attached to a suitable inert surface for sustained activity.

3. The bioprocess as claimed in claim 1, wherein the (per)chlorate and/or nitrate containing matrix is contacted with propellant wastewater containing perchlorate, ammonia, and high salt, at acidic or alkaline pH, wherein the high salt concentration is >15%.

4. The bioprocess as claimed in claim 1, wherein a (per)chlorate contaminated soil leachate is contacted with the consortium.

5. The bioprocess as claimed in claim 1, wherein the nutrient in step (a) is mineral salt medium containing (g/L water) $K_2HPO_4$—0.22, $KH_2PO_4$—0.22, $(NH_4)_2SO_4$—0.22, $MgSO_4.7H_2O$—0.05, $CaCO_3$—0.005, $FeSO_4.7H_2O$—0.005, $KClO_4$—1.5 g/L and a trace metal solution.

6. The bioprocess as claimed in claim 1, wherein the matrix prior to contacting with the consortium has perchlorate in the range of ≥5 g/L.

7. The bioprocess as claimed in claim 6, wherein reduction of nitrate and perchlorate using the consortium is carried out in the presence of ammonium.

8. The bioprocess of claim 2 wherein the inert surface comprises glass, plastic, ceramic.

9. The bioprocess of claim 1 wherein the contaminated matrix is a solid matrix with a salinity up to 15%, a pH in the range 4 to 10 and perchlorate up to 5 g/L.

10. The bioprocess as claimed in claim 6, wherein reduction of nitrate and perchlorate using the consortium is carried out in the absence of ammonium.

* * * * *